(12) United States Patent
Müller

(10) Patent No.: US 7,455,967 B2
(45) Date of Patent: Nov. 25, 2008

(54) DEVICE FOR ANALYZING CHEMICAL OR BIOLOGICAL SAMPLES

(75) Inventor: Ralph Müller, Eberbach (DE)

(73) Assignee: Axaron Bioscience AG, Heidelberg (DE)

( * ) Notice: Subject to any disclaimer, the term of this patent is extended or adjusted under 35 U.S.C. 154(b) by 369 days.

(21) Appl. No.: 10/333,884

(22) PCT Filed: Jul. 25, 2001

(86) PCT No.: PCT/EP01/08618

§ 371 (c)(1),
(2), (4) Date: Sep. 10, 2003

(87) PCT Pub. No.: WO02/08457

PCT Pub. Date: Jan. 31, 2002

(65) Prior Publication Data

US 2004/0053327 A1    Mar. 18, 2004

(51) Int. Cl.
*C12Q 1/68* (2006.01)
*C12M 1/36* (2006.01)
*G01N 15/06* (2006.01)

(52) U.S. Cl. ............ 435/6; 435/283.1; 435/287.2; 435/288.5; 422/68.1; 422/82.05

(58) Field of Classification Search .............. None
See application file for complete search history.

(56) References Cited

U.S. PATENT DOCUMENTS

| | | | |
|---|---|---|---|
| 3,932,131 A | 1/1976 | Rolfo-Fontana | 23/230 R |
| 4,090,848 A | 5/1978 | Naono | 23/253 R |
| 4,144,452 A | 3/1979 | Harte | 250/302 |
| 4,740,313 A | 4/1988 | Schoendorfer et al. | 210/651 |
| 5,143,854 A | 9/1992 | Pirrung et al. | 436/518 |
| 5,192,412 A * | 3/1993 | Kambara et al. | 204/612 |
| 5,427,948 A | 6/1995 | Diers | 435/312 |
| 6,139,757 A * | 10/2000 | Ohmura et al. | 210/797 |
| 6,368,865 B1 * | 4/2002 | Dahl et al. | 436/37 |

(Continued)

FOREIGN PATENT DOCUMENTS

DE    19828837    6/1998

(Continued)

OTHER PUBLICATIONS

Fodor et al. "Light-directed, spatially addressable parallel chemical synthesis." *Science*. Feb. 15, 1991;251(4995):767-73.

*Primary Examiner*—BJ Forman
(74) *Attorney, Agent, or Firm*—Lahive & Cockfield, LLP

(57) ABSTRACT

The present invention relates to a method, and to a corresponding device, for analyzing chemical or biological samples in which chemical or biological samples and/or targets (probes) are applied in the form of individual defined spots to an outer cylindrical jacket surface of a support, or are aliquoted in the form of fluid droplet into drill holes whick are chased in the jacket surface of the support. The support is inserted into a recess in a retainer, which recess is essentially complementary to the cylindrical jacket surface, the samples and/or targets are acted upon by way of physical and/or chemical interactions, and the correspondingly modified spots are then analyzed. The present invention provides an analytical system which provides unambiguously defined reaction volumes, which is easy to standardize and which can be automated to a high degree.

20 Claims, 6 Drawing Sheets

U.S. PATENT DOCUMENTS 6,767,706 B2 * 7/2004 Quake et al. ................ 435/6

FOREIGN PATENT DOCUMENTS

| DE | 19852835 | 5/2000 |
|----|----------|--------|
| JP | 62-069164 | 3/1987 |
| WO | WO 87/07384 | 12/1987 |
| WO | WO 90/15070 | 12/1990 |
| WO | WO 91/07087 | 5/1991 |
| WO | WO 92/10092 | 6/1992 |
| WO | WO 92/10587 | 6/1992 |
| WO | WO 92/10588 | 6/1992 |
| WO | WO 00/40334 * | 7/2000 |

* cited by examiner

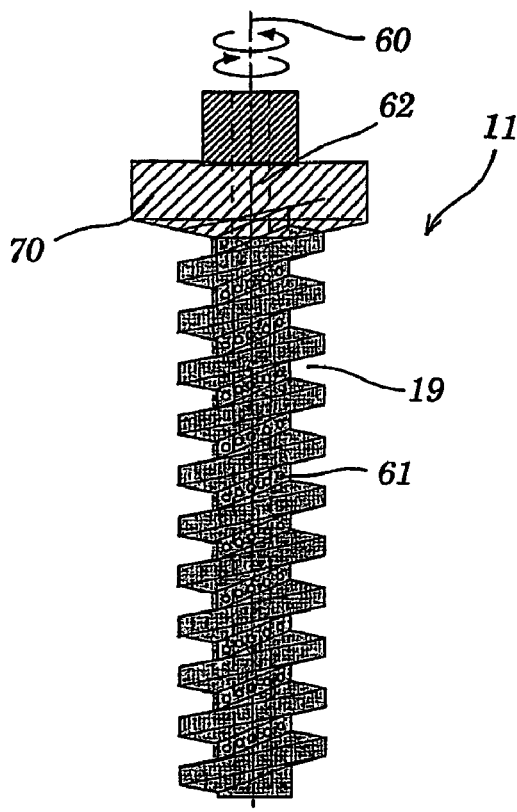
Fig. 11
Fig. 12
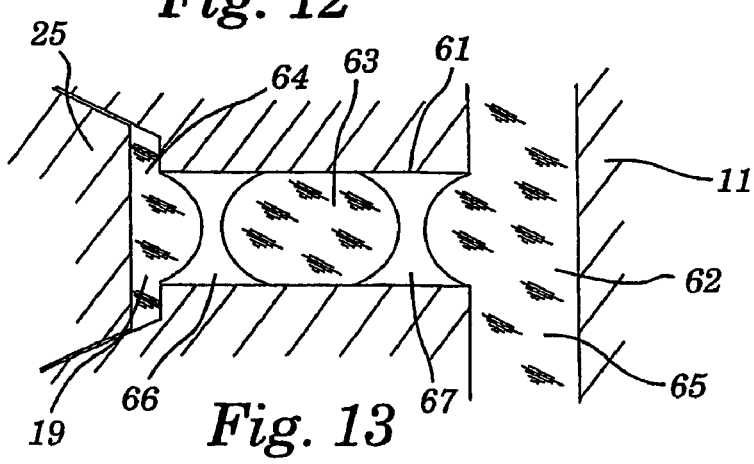
Fig. 13
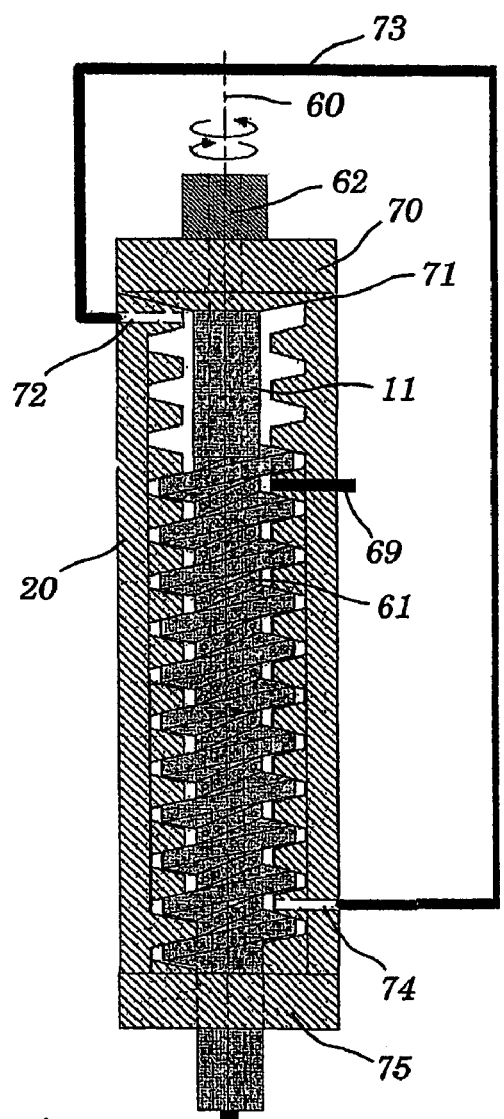
Fig. 14

DEVICE FOR ANALYZING CHEMICAL OR BIOLOGICAL SAMPLES

The invention relates to a method and to a device for analyzing chemical or biological samples. In particular, the present invention relates to a novel support system for chemical or biological assays, in particular for use in DNA or RNA analysis, with it being possible for the biological probes or samples to be immobilized to be, for example, DNA, RNA, cDNA, oligonucleotides or PNA oligos.

Discovering new genetic information, or recognizing known genetic information, is an elementary molecular biological task, to achieve which a large number of different methods have already been proposed. High-throughput detection techniques are increasingly coming into use in order to make it possible to handle the enormous amount of genetic information in biological systems. A popular representative of these techniques is the DNA CHIP, or the DNA array, which, by using a high density of applied probes (>1 000 per cm$^2$), enables many thousand samples to be analyzed simultaneously. In this connection, use is principally made of a conventional glass microscope slide whose planar surface is coated with DNA-binding reagents. In connection with genomic applications, the probes which have been loaded on and bound are termed target sequences or targets. The targets have frequently already been identified genetically, which means that the gene sequence, and also in many cases the physiological function of the targets in the relevant organism, are known. This prior target information can be used to interrogate new systems, to establish relationships or differences, to perform classifications or to investigate the biological purpose and function of the system. The biol. system to be investigated is applied, as the sample, to the slide and then hybridized. This involves the target DNA, which is fixed to the carrier surface, and the sample DNA, which is complementary to the target, locating each other and entering into a bond. If the sample DNA is, for example, labeled with a dye, the target can then subsequently be detected and the site or the position on the DNA array can be used to classify, and thus obtain preparatory information on, the target. Hybridization to a DNA array can be used for qualitatively and/or quantitatively analyzing complex genetic information.

Northern and Southern blots, and also in-situ hybridization, are classical applications of this nature. For this, the samples are as a rule prepared appropriately and investigated using defined DNA targets. Substances, i.e. what are termed labels, which can be identified using suitable detection methods are employed for labeling the samples. Radioactive labels, and also chemiluminescent or fluorescent labels, are particularly widely employed. In this connection, fluorescence methods, in particular, have a high standing in chemical and biological analysis and diagnosis. These methods are very powerful detection methods which can be performed without using any radioactivity and, if necessary, without using any toxic substances. There nowadays exist sensitive detection systems which even make it possible to detect individual fluorescent molecules. In addition, a large number of very different fluorescent dyes are available, such that it is possible to have recourse to suitable fluorescent labels for most wavelength ranges in the visible spectrum and also in the adjoining ultraviolet or infrared spectral range. It is frequently even possible to use several fluorescent dyes, having different excitation and/or emission wavelengths, in parallel when carrying out a measurement.

In the present instance, a solid support is understood as being a material which has a rigid or semirigid surface. Supports of this nature can, for example, be particles, strands, in particular fiber bundles, spherical bodies, such as spheres or spherules, precipitation products, gels, sheets, tubes, receptacles, capillaries, disks, films or plates. Flat supports are normally used.

As a result of progressive miniaturization, it has by now become possible to reduce the DNA spaces substantially such that it is nowadays possible to arrange a large number of spaces, which can be distinguished both from a point of view of process technology and measurement technology, on a single support. In imitation of semiconductor technology, reference is therefore made to chips, in particular biochips, gene chips, etc. The targets are bound to the support at as high a density as possible. In particular, the application of photolithographic manufacturing techniques derived from semiconductor technology has led to decisive advances in the production of these chips. The principle is based on light-directed chemical solid phase synthesis in which photolithographic masks image the spaces (cf., for example, Fodor et al., "Light-directed, spatially addressable parallel chemical synthesis", Science, vol. 251, 767-773 (1991)). This method is particularly advantageous when the target DNA is to be synthesized from individual nucleotides in situ on the support. Thus, a particular building block can be selectively added on to the targets which are in the process of being synthesized on particular spaces while the probes on the remaining spaces remain unaffected. In this way, it is possible to produce, on a large scale, DNA oligochips which, when used combinatorially, enable new sequences to be discovered. In order to recognize sought-after sequences, the oligosynthesis chip requires elaborate pattern recognition. Methods for this purpose are described in detail in international patent applications WO 90/15070, WO 91/07087, WO 92/10092, WO 92/10587, WO 92/10588 and in U.S. Pat. No. 5,143,854.

In contrast to the synthesis arrays, spotting arrays, in which the previously produced DNA sequence is transferred in complete form to the support, are increasingly being used in practice. Different methods, such as inkjet spotting, solid pin spotting or microprinting, are used for applying the DNA solution. Arrays of this nature are suitable for a large number of applications, starting with the sequencing of DNA and proteins and proceeding all the way to DNA finger-printing and disease diagnosis. Commercial biochips, containing a large number of different cDNAs for hybridization, are by now being offered for sale. These cDNAs are nucleic acid sequences having lengths of from about 200 to 600 base pairs (bp. It is precisely in the area of gene expression profiling, that is identifying the state of activity of genes of interest, that the spotting chip comes into its own. In this connection, a control DNA pool is always compared with a stimulated DNA pool and changes in gene activity thus determined for the given problem or the relevant biological model. Chip technologies are increasingly being employed, in particular, for finding relevant biomolecules which, for example, have a key role in the organism.

While very many different substances or molecules can be immobilized on these planar chips, DNA arrays which are known today still suffer from problems in connection with handling and applicability. The essential reason for these problems is the lack of reproducibility of the overall process, which consists of many individual steps.

In addition, the lateral exchange of substances in the sample liquid which has been applied to the chip is controlled solely by diffusion, which means that there is no guarantee, at least within a practicable total period of measurement, that each species in the sample liquid is able to interact with each sample species which is immobilized on the chip surface.

Apart from the abovementioned planar systems, German patent application DE 198 28 837 A1 describes the use of hollow minicylinders as a solid phase for ELISA tests in microtiter plates. However, this publication does not disclose any application of individual, defined spots to these hollow minicylinders.

Finally, U.S. Pat. No. 5,427,948 discloses a device for hybridizing DNA fragments, with the DNA fragments being immobilized on a membrane. The individual spots are applied to the planar membrane such that the preparation of the arrays and their analysis essentially corresponds to the methods which are known from conventional planar biochips. The membrane is only inserted into a sealable treatment drum, which consists of two cylinders which are nested one within the other, for the purpose of implementing the actual hybridization. It is not possible to perform an automatable process sequence using such a device.

The object of the present invention is therefore to provide an improved method, and a corresponding device, for analyzing chemical or biological samples so as to ensure a process sequence which can be standardized and can be fully automated. In addition, it is intended that the method and the device of the invention should ensure that a sample volume which is to be analyzed can interact reliably with any probe.

This object is achieved by means of the method of the present claim 1 and the device of the present claim 16. The dependent claims relate to advantageous developments of the method according to the invention and the device according to the invention.

The present invention accordingly relates to a method for analyzing chemical or biological samples in which chemical or biological samples and/or targets (probes) are applied, in the form of individual, defined spots, to an outer cylindrical jacket surface of a support, or are aliquoted, in the form of fluid droplets, into drill holes which are chased in the jacket surface of the support, the support is introduced into a recess in a retainer, which recess is essentially complementary to the cylindrical jacket surface, the samples and/or targets are acted upon chemically or physically, and the spots are then analyzed.

The core of the invention is consequently the use of a novel support system for investigating chemical or biological samples, which support system is characterized by a cylindrical geometry, with it being possible to apply, for example immobilize, substances on the functionalized jacket surface of the cylinder or in radial drill holes which are chased in the cylinder jacket. Cooperation with a complementary retainer results in an analytical system which uses clearly defined reaction volumes and which, in contrast to planar biochips, is easily standardizable and highly automatable.

In that which follows, reference is usually made, for the sake of simplicity, to "spots", with this then being able to mean, depending on the context, either the samples which have been applied to the jacket surface or the fluid droplets which have been introduced into the drill holes.

For example, for the purpose of applying the spots, the support can be conveyed, in a combined translatory and rotatory movement, past a loading device such that the spots are arranged along helical tracks on the jacket surface. It is possible, for example, to use highly precise threaded spindle-nut drives, which are known per se, for this purpose. Each spot can then be located unambiguously on the jacket surface or in the drill hole. Preference is given to using a loading device which is arranged at the entrance to the retainer for applying the spots and to introducing the support into the retainer while the spots are being applied such that, immediately afterward, reaction fluids can be flushed over the jacket surface. However, it is also possible to use an external loading device and to first of all apply all the spots before introducing the support into the retainer.

After that, the substances which have been applied in the spots can be subjected to suitable chemical or physical action, for example DNA target spots can be hybridized with sample DNA contained in sample fluids which are led over the jacket surface and subsequently analyzed.

If, in a variant of the invention, radial drill holes which communicate with a central drill hole which is provided in the support are chased in the jacket surface, it is then possible, for the purpose of chemically and/or physically acting upon the samples or targets, to mix the fluid droplets which have been introduced into the drill holes with a fluid which is present in the central drill hole and/or between the jacket surface and the support. It is thus possible, simultaneously or in a chronologically staggered manner, to mix at least two different fluids with the sample fluid droplets. A solid core can also be introduced into the central drill hole, which core then forms a floor for the radial drill holes which are chased in the jacket surface.

In order to analyze the spots, the support is conveyed, in a combined translatory and rotatory movement, past a detection device. In this connection, the direction of movement of the support is advantageously reversed such that the support is removed from the retainer. The previously applied spots are then conveyed past the detection device along the same helical track, thereby facilitating the standardization and automation of the processes.

According to a particularly preferred embodiment of the invention, target spots are introduced into at least one helically recessed thread track which is chased in the jacket surface of the support. The targets are consequently applied, like conventional planar biological arrays, on the surface of a support. The support is then screwed into the retainer, which is provided with a corresponding counterthread, and at least one sample fluid is conveyed through a channel which is defined along the track. At the same time, the substances which are present in the sample fluid can interact with the probes on the support and, in the case of DNA analyses, hybridize with the probes, for example. A particular advantage of the method according to the invention, as compared with the conventional use of planar arrays is that the bolt/nut geometry which is realized by the support and retainer defines a reaction volume which is very small in cross section to the track. Samples and targets can therefore proceed very rapidly, even when the processes are controlled simply by diffusion, thereby enabling measuring times to be short. At the same time, transporting the sample fluid through the helical track ensures that the sample volume to be analyzed can reliably interact with each probe. Finally, the support is once again screwed out of the retainer and the interactions which have occurred between the probes and the sample fluid are detected, preferably during the unscrewing procedure.

In this connection, the sample fluid can be conveyed through the channel by the displacement effect of the support which results on introducing the support into the retainer. For this, and prior to introducing the support, the sample fluid is aliquoted, either manually, using a pipetting robot or using suitable fluid ducts which are integrated into the retainer, into the interior of the retainer, and a communicating fluid connection is established between the channel and the interior. However, it is also possible to use a pump to convey the sample fluid, and, where appropriate, other reaction fluids, through the channel. It is also possible to aspirate the fluids at the end of the channel and, where appropriate, return them to the channel entrance for a further transit.

Advantageously, the targets are immobilized in the channel of the support or in the radial drill holes before the samples are analyzed. Conventional techniques, which are known from planar arrays, can be used to do this. The targets can be applied, for example, as defined spots when the support is being screwed into the retainer. By controlling the process with a computer, each probe spot is assigned to a defined position in the thread of the retainer, which position can be referred to, when analyzing the measurement, for identifying the interaction which has occurred at this site between target and sample. Probe spots are preferably immobilized on the tracks, that is, for example, the thread, in the form of a linear array. The target spots preferably have a diameter between 10 and 200 μm and are preferably applied at a length density of from 10 to 500 spots/cm, particularly preferably of from 25 to 200 spots/cm.

When using a support having radial drill holes, it is also possible to apply highly ordered molecular monolayers on the inner wall of the drill holes. Using a method which follows the conventional Langmuir-Blodgett technique, a liquid meniscus is allowed to penetrate into the drill holes, whose inner wall is hydrophilic, such that the liquid is able to wet the inner wall. A monomolecular layer of amphiphilic molecules can be formed on the surface of the liquid. This layer is transferred to the inner wall of the drill hole when the liquid meniscus is withdrawn from the drill hole.

The method according to the invention is particularly suitable for DNA hybridization or RNA hybridization. Preference is therefore given to immobilizing DNA/RNA targets on the support and hybridizing them with DNA/RNA samples which are present in the sample fluid.

It is particularly advantageous, according to the invention, to use fluorescence-labeled samples, such that interactions between probes and samples, or the electrophoretic fractionation of the samples, can be analyzed optically. For the labeling, it is possible to use any fluorescent dyes which can be coupled chemically to the substance to be labeled. It is possible, for example, to integrate an excitation and detection system into the retainer for this purpose.

A variant of the support system makes it possible to use the system in gel electrophoresis. As a result of the massive amount of information contained in biological systems, DNA sequencing, in particular, requires a highly parallel approach. DNA sequencing in shallow gel electrophoresis chambers (flat gel) having up to 100 parallel analytical lanes, or, for an even higher throughput, DNA separation in gel capillaries, having about the same degree of parallelization but a shorter analytical time, are currently popular. A special polymer solution, which effects the fractionation of the prepared DNA is used in the gel capillaries. However, the polymer solution does not permit the achievement of separation efficiencies which are as high as those achieved by crosslinked gels which are customary in the case of the flat gels. In capillary electrophoresis, the solution is removed from the capillary under pressure after the analysis and in this way prepared for the next sequence run; crosslinked gels can no longer be removed from the capillary.

It is now proposed, according to the invention, to use a support in whose jacket surface several parallel, gel-coated tracks are chased, to apply the sample spots to defined regions on the tracks, to separate the substances contained in the sample spots from each other electrophoretically, after the support has been introduced into the retainer, and then to detect the separated substances. The tracks can, for example, run essentially parallel to the jacket line of the support. However, they can also run helically on the jacket surface of the support such that a longer running distance is available with the support having the same external dimensions. It is also possible to make numerous helical tracks which run in parallel, in a multihelical arrangement. If use is made of a helical support which is designed in a multihelical manner it is then possible to make capillary tracks which can be cleaned automatically using a counterthread rim, such that capillaries can be combined with crosslinked gels, thereby combining a short analysis time with high separation quality. Furthermore, it is possible to achieve, in the multihelical arrangement, a high degree of parallelization of, for example, more than 600 helical gel tracks on a support having a radius of 1 cm. It is also possible to achieve optical excitation and detection in a simple manner on the cylindrical support which is moved at constant rotational velocity. In this way, it is possible to determine approximately 10 times more sequence data per unit of time than do the highest throughput appliances used in the current state of the art.

The present invention also relates to a device for analyzing chemical or biological samples, which device is particularly suitable for implementing the method according to the invention. The device comprises a support which exhibits an essentially cylindrical jacket surface which, on at least a part of its surface, can be functionalized such that chemical or biological targets or samples can be applied, a retainer which exhibits an essentially cylindrical recess into which the support can be inserted, and a drive device for inserting the support into the retainer and for withdrawing the support from the retainer.

Advantageously, means are also provided for conveying fluids through at least one channel which is defined between the jacket surface of the support and the inner surface of the recess. The means for conveying fluids advantageously comprise at least one fluid reservoir and one pumping device which can be used for conveying the fluid through the channel. According to one possibility, the means for conveying fluids are formed by the support, acting as a piston, and the retainer recess, serving as the fluid reservoir. For this, the support can comprise, at its front side, a threadless cylindrical section whose outer diameter essentially corresponds to the inner diameter of the recess in the retainer. A passage which communicates with the thread of the support, on the one hand, and, on the other hand, with the retainer recess when the support is screwed in, can be chased in the threadless cylindrical section. When the support is screwed in, the sample fluid is displaced out of the recess and flows through the passage into the thread channel. The means can be recovered using a sample collecting system at the outlet of the support and recirculated cyclically. According to a second possibility, the means are applied in an external hose system and pumped through the helical channel using an external pumping system. The means can be recovered at the outlet of the support using a sample collecting system and recirculated cyclically.

According to a variant of the device according to the invention, the constituent region of the support jacket surface which can be functionalized can be designed as radial drill holes in the jacket surface. These drill holes can be blind drill holes which form wells in the jacket surface. However, the radial drill holes preferably communicate with a central drill hole which runs along the longitudinal axis of the support. Defined quantities of sample fluids can be introduced into these radial drill holes, with the sample fluids being retained in the drill holes by capillary forces.

Means for applying the targets or samples in the form of individual defined spots are also advantageously provided, with it being possible for the means to be designed, for example, as pins which can be used to apply minimal quantities of fluid at defined sites on an appropriately functionalized surface or to introduce these quantities of fluid into a functionalized drill hole.

At least one functionalizable track or drill hole is preferably chased in the jacket surface of the support. The track (or the tracks) can run essentially parallel to the jacket line of the support. In this case, the inner wall of the retainer can be smooth. Such a support is suitable, in particular, for electrophoretic investigations or for DNA sequencing. Subordinately, it is possible to provide a rim possessing inner teeth which, on further advancement, is able to remove the crosslinked gels in from the tracks. However, the tracks can also run helically on the jacket surface of the support. Using this geometric arrangement, it is possible to achieve a high channel length which permits a significantly larger number of laid-down targets than does a planar surface, for example a number which is twice as high.

According to an advantageous embodiment, the helical track on the jacket surface of the support forms a thread track and the cylindrical recess in the retainer exhibits a complementary counterthread which is designed such that, after the support has been screwed into the retainer, a channel, through which the sample fluid can be conveyed, is formed along the thread track. The thread track advantageously possesses possesses an essentially rectangular or trapezoidal thread profile or is designed as a metric ISO thread, round thread or pipe thread.

Preferably, the driving device for automatically screwing the support into the retainer and for unscrewing from the retainer comprises a stepping motor, a servomotor or a synchronous motor. The motor can be coupled to the support by way of a transmission. When the support possesses tracks which essentially run virtually axially, it is sufficient for the driving device to push the support axially into the retainer. In this case, a helical movement is only required within the context of the system play, depending on the thread pitch. A linear drive or a hydraulic system can be used as the drive unit.

Advantageously, the support and/or the retainer and/or the core which can be introduced into a central drill hole in the support can be kept at a temperature within the range from 0° C. to 100° C.

The thread track of the support, or the internal wall of the radial drill hole, preferably exhibits a surface which is made of a material which is selected from the group consisting of glass, in particular quartz glass, carbon, plastics (in particular fluorescence-poor polymer material) or resins, such as polytetrafluoro-ethylene, polyvinylidene difluoride, polystyrene or polycarbonate, PMMA, including membrane-forming materials, such as nitrocellulose or nylon, and also monomolecular films of amphiphilic molecules, such as Langmuir-Blodgett films which, for reasons of stability are preferably polymerized, metal, in particular gold, platinum, chromium or copper, semiconductor materials, such as Si, Ge, GaAs or GaP, preferably in monocrystalline form, and ceramics. The supports can be made of a homogeneous material; in particular plastics are preferably used as a homogeneous material which is modified or functionalized throughout, such that no further surface treatment is required; however, the supports can also be made of composite materials in which the surface fulfills the abovementioned criteria. Preference is given to surfaces which possess functional groups such as carboxyl, amino or hydroxyl groups. Particular preference is given to glasses, $SiO_2$ and semiconducting materials, in particular Si and modified Si. The loading can be effected by means of flushing the surface reagents into the sample channel and, possibly, by means of a subsequent drying operation, by introducing the support into a displacer-retainer.

Depending on the probe to be applied, the surface of the thread track of the support can additionally possess a covering layer, which is preferably hydrophobic, or what are termed spacers and/or linkers. The interaction, for example the degree of mobility, between a probe and a sample, for example a hybridization sample, can be affected by the length and nature, for example the polarity, of a spacer. In this connection, it is advantageous to optimize the spacer with a view to making the probe as accessible as possible. Examples of suitable spacers are bifunctional compounds, such as diamines, diacids, for example dicarboxylic acids, or ethylene glycol oligomers, heterobifunctional compounds, such as amino acids, arylacetylenes, functionalized head groups of polymerized Langmuir-Blodgett films, lectins, biotins, avidins or streptavidins or combinations thereof. Spacers can also be synthesized from several moieties which are linked to each other by means of covalent and/or noncovalent bonds. Examples of covalently linkable moieties of a spacer are heterobifunctional elements, such as amino acids, for example 6-amino-capric acid or [lacuna]-aminobutyric acid, several of which can be bonded to each other for the purpose of elongating a spacer. Examples of moieties of a spacer which can be linked noncovalently are molecules between which it is possible to form affinity bonds, as between biotin and avidin or streptavidin or their analogs, or between DIG and anti-DIG. Spacers can possess one or more binding sites for the probes which are to be applied. As a rule, the above-discussed hetero-bifunctional elements possess one such binding site for oligonucleotide probes, for example, whereas molecules which form affinity bonds, such as avidin or streptavidin, possess several binding sites. The latter molecules can lead to an advantageous increase in the immobilized probes per unit area. Spacers can also possess variable binding sites which offer different bonding possibilities depending on configuration. This applies, in particular, to affinity bonds, whose binding affinity can vary depending on the configuration of the participating binding partners.

Bonds between the surface of the support and the probes, for example polynucleotide targets, can be covalent or noncovalent (for example electrostatic or coordinate). Covalent bonds are preferred. Frequently, the probes or spacers are not bound directly to the functional groups which may possibly be naturally present on the surface. In these cases, the functional groups which are present are first of all modified, for example by introducing a more expedient functional group. The skilled person is familiar with methods which are suitable for this purpose, depending on the surface material and the desired bond. Glassy surfaces of supports according to the invention are preferably functionalized by forming siloxane bonds. In this connection, silanes, for example compounds possessing trichlorosilyl or trialkoxysilyl groups, are bonded to the hydroxyl groups, which are naturally present, of the Si—OH functionalities. The probes or spacers, for their part, are bonded to more expedient functional groups which are provided by the silanes. Epoxy groups can be introduced, for example, using 3'-glycidoxy-propyltrimethoxysilane and amino groups can be introduced, for example, using aminopropyltriethoxy-silane. Diepoxides or cyanogen bromide can likewise be used for functionalizing the surface. In the same way, the formation of acetal from alcohols using aldehydes or ketones, such as the formation of thioacetal, or iodothiophosphate bonding, can be used for the covalent bond.

On the other hand, probes or spacers can be bound, without any further functionalization, to some surfaces, in particular to special polymers. These include, for example, polyvinylidene difluoride possessing aminopropyl groups, or particular Langmuir-Blodgett films in which the head groups can even function as spacers.

It is also possible to apply what are termed multicoatings, i.e. several different layers, to the support.

In addition, the surface of the support material and/or the coatings can be modified by physical methods such as plasma treatment or sputtering.

Advantageously, the retainer additionally possesses an excitation and detection device for investigating the chemical or biological probes or samples. The excitation and detection device is preferably arranged between the drive unit and the retainer, such that the tracks, or the single helical track, can be analyzed when rotating the support out of the retainer.

In the case of electrophoretic measurements, the screw device is arranged vertically; in this case, the excitation and detection unit is arranged in the lower region of the retainer. The samples are then applied at the upper end of the support and migrate downward in a gel along an electrical potential gradient. In this case, the detection system records the migration time of the individual bands. The individual channels or tracks can be investigated sequentially by rotating the support in the retainer.

Preference is given to using optical investigation methods, with chemiluminescence measurements or fluorescence measurements being preferred. For the fluorescence measurement, the fluorescence-labeled samples are advantageously excited with a focused laser beam and the emitted fluorescent light is detected using a photomultiplier or a photodiode. The excitation and/or detection can take place confocally in order to fade out interfering fluorescent light from the solution in the channel or from the support. If different fluorescent labels are used, the detection can also take place spectrally or in a time-resolved manner such that it is possible to draw conclusions with regard to the individual constituents of the bound labels. If a complete integration of an excitation and detection system into the retainer is not desirable, it is also possible to use fiber optics in order to conduct light from and to an external detection system. The device according to the invention therefore preferably possesses an excitation and detection arrangement which comprises means for simultaneously emitting light of differing wavelength and means for simultaneously detecting light of differing wavelengths and/or for detecting optical signals in a time-resolved manner. The variant of the device according to the invention in which the support is provided with radial, functionalizable drill holes is also particularly suitable for carrying out absorption measurements. For example, light can be conducted, by way of the central drill holes, into the individual radial drill holes and onto a detector which is arranged outside the cylindrical jacket of the support.

The present invention finally also relates to the use of the device according to the invention for analyzing DNA or RNA, with the biological probes or samples to be immobilized being selected from the group comprising DNA, RNA, cDNA, oligonucleotides or PNA oligos.

In this connection, a preferred use is directed toward screening or quantifying samples for particular ligands (target sequences) which bind with high affinity to immobilized oligonucleotides/polynucleotides or synthetic analogs, cDNA, ccDNA or cRNA. For this, a solution containing labeled samples is conveyed through the channel along the helical track of the support. Unbound ligand is removed by rinsing the channel. Ligands which have bound to the immobilized probes as a result of adequate affinity are detected when unscrewing the support from the retainer.

Hybridization to DNA spots containing immobilized oligonucleotides/polynucleotides or synthetic analogs, cDNA, ccDNA or cRNA, where appropriate with subsequent primer extension, for the purpose of sequencing, gene expression analysis, typing viruses and microorganisms, and mutation analysis, are also regarded as being preferred uses.

Samples can be obtained in a conventional manner. Usually, at least parts of nucleic acids of interest are isolated from a tissue sample. In the case of genomic investigations carried out on eukaryotes, any tissue is suitable provided it contains cell nuclei. Blood, lymphocytes derived from peripheral blood or a buffy coat, skin, hair or semen are common sample sources from which both DNA and RNA can be isolated. Body fluids, such as serum, sputum, urine, peritoneal fluid, pleural fluid or bronchoalveolar lavage are suitable for isolating nucleic acids from viruses, bacteria or fungi. On the other hand, mRNA can only be isolated from those cells or tissues in which the desired mRNA is transcribed.

The skilled person is familiar with a large number of methods for isolating nucleic acids. Only a few will be briefly outlined here by way of example.

In order to isolate genomic DNA, the cells can be lysed, for example under the action of detergents and/or proteinases, proteins can be removed and the DNA can be isolated, for example by precipitating with known organic solvents. It may also be appropriate to carry out a chromatographic separation, for example using commercially available spin columns. Similar methodological procedures are used when isolating total RNA. Polyadenylated mRNA can in turn be isolated from this total RNA by using systems which are based on oligo-(dT). Expert knowledge will determine the choice of an expedient protocol. RNA can then be transcribed into cDNA by means of reverse transcription. DNA or cDNA can be amplified using various methods which are known to the skilled person.

The complexity of a sample, i.e. the diversity and sequence length of the nucleic acids present in it, can be decreased, prior to the investigation, by enriching those nucleic acids which contain the targets. If a subset of mRNA is to be investigated, it is possible, for example, to hybridize the total mRNA with the immobilized nucleic acid polymers, then to treat with RNase A in order to digest single-stranded regions, and subsequently to denature the double-stranded hybrids, in order, finally, to remove the nucleic acid polymers, such that there then remains a pool of mRNA whose complementarity to the immobilized nucleic acid polymers has been increased. The skilled person is familiar with other methods which serve the same purpose and which can be used within the context of the present invention, such as digesting double-stranded nucleic acids with RNase H using suitable hybridization probes.

In addition, the device according to the invention can be used for protein analysis and for drug screening, with the biological probes or samples in this case comprising proteins, in particular antibodies, receptors or ligands. It is likewise possible to use the device according to the invention for allergy diagnosis, with the biological or chemical samples in this case being selected from the group comprising antigens, haptens or allergens.

Finally, the present invention relates to the use of the device according to the invention as a DNA computer. It has already been demonstrated that oligonucleotides which are immobilized on the surface of a support, for example by specifically hybridizing with particular samples or as a result of specific enzymic digestion, can be used for solving mathematical problems. Reference may be made, at this point, by way of example, to the review article by L. M. Adleman "Computing with DNA", Scientific American 279(2): 54-61, 1998. Special applications are described, for example, in Liu et al., "Progress toward demonstration of a surface based DNA computation: a one word approach to solve a model satisfiability problem", Biosystems 51(1-3): 25-33, 1999 or Smith et al., "A surface based approach to DNA computation", Journal of Computational Biology, 5(2): 255-267, 1998. A large number of the methods which are described there can also be implemented using a linear oligonucleotide/polynucleotide array on a cylindrical or helical support of the device according to the invention.

The present invention is described in more detail below while referring to the implementation examples which are depicted in the attached drawings.

In the drawings:

FIG. 11 shows another variant of a support of the device according to the invention;

FIG. 12 shows a view from above onto the support shown in FIG. 11;

FIG. 13 shows a detailed cutout of the support shown in FIG. 11, which is arranged in a complementary retainer; and FIG. 14 shows a variant of the support shown in FIG. 11 in a corresponding retainer.

Figure 1:
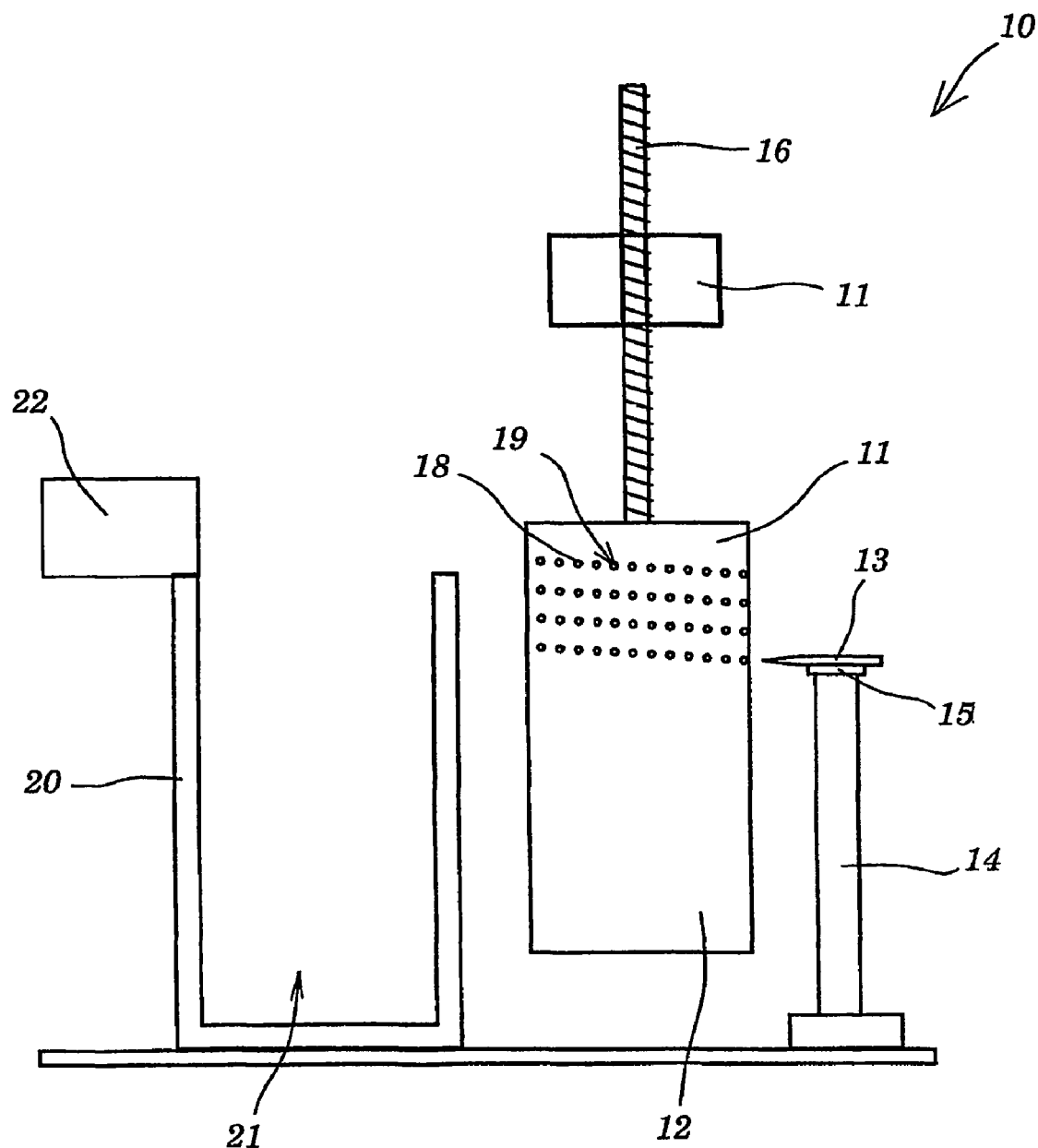
FIG. 1 shows a first embodiment of a device according to the invention.

FIG. 1 shows a device according to the invention for analyzing chemical or biological samples, which device is designated in its entirety by the reference number 10. The device 10 exhibits a support 11 having a cylindrical jacket surface 12. The jacket surface 12 is functionalized such that chemical or biological targets can be applied and immobilized using a loading device 13, as depicted in more detail in FIG. 4. The loading device 13 can, for example, be a small tube having a tapering tip, which device has a reservoir from which substances which act as probes, and which are customarily dissolved, dispersed or emulsified in a liquid, can be transferred to the functionalized surface, for example by way of capillary forces. The loading device 13 can, for example, be fixed on a rotatable and/or displaceable arm 14 and moved in the direction of the jacket surface 12 by means of an advancing arrangement 15.

A spindle 16 of a linear drive 17 (as is marketed, for example, by Haydon Switch and Instrument, Inc.) is connected to the support 11 such that this latter can be set in a combined rotatory and translatory movement. In this movement, the loading device 13 can be used to apply spots 18 along a helical track 19 on the jacket surface 12.

The device 10 according to the invention additionally comprises a retainer 20 which exhibits an essentially cylindrical recess 21 over which the support 11 can be positioned using a robot arm (not depicted). The support 11 is inserted into the retainer 20 using the drive 17. A sample liquid and, where appropriate, other reaction liquids, are then conveyed through an annular channel which is defined between the jacket surface 12 and the inner wall of the recess 21. Sucking-off arrangements (not depicted here), which lead away the sample liquid after it has flowed through the annular channel, can be provided in the upper region of the retainer 20.

The interaction of the target spots 18, which are immobilized on the jacket surface 12, and the substances in the sample liquid can be detected when withdrawing the support 11. An excitation and detection device 22, which is depicted diagrammatically in FIG. 1, is provided for this purpose in the upper region of the retainer 20. The support 11 is withdrawn by the drive 17 once again in a combined translatory and rotatory movement such that all the spots 18 on the track 19 are conveyed past the detection device 22.

Advantageously, the support 11 and/or the retainer 20 can be heated and cooled. Preference is given to being able to set a temperature of from 10° C. to more than 95° C., such that the device can also be used for carrying out amplification reactions, for example PCR.

Figure 2:
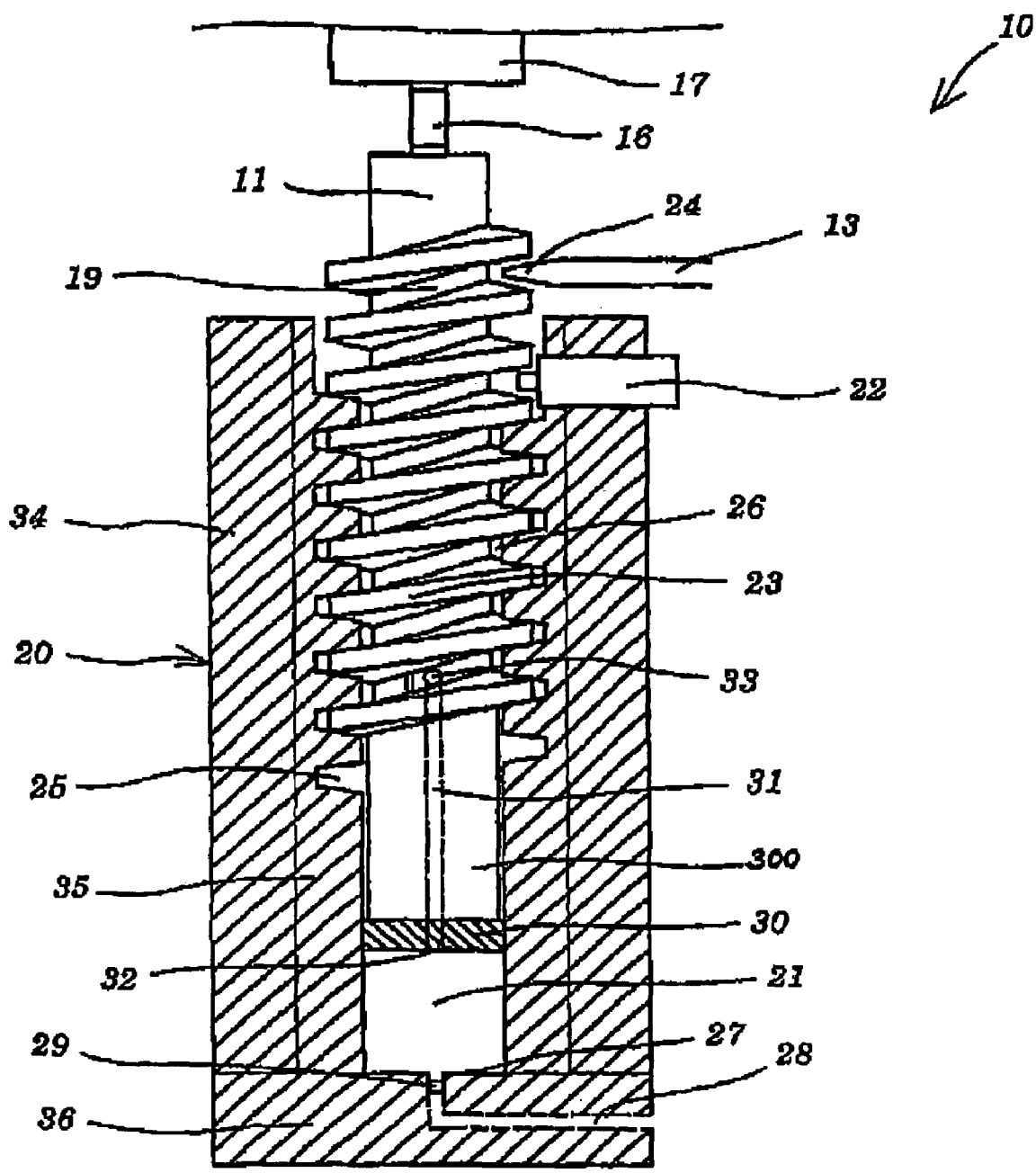
FIG. 2 shows a second embodiment of a device according to the invention.

FIG. 2 shows a second embodiment of a device 10 according to the invention. Elements which have already been explained in connection with the embodiment shown in FIG. 1, or which exert a similar function, are denoted by the same reference numbers.

The device shown in FIG. 2 exhibits a cylindrical, helically shaped support 11 which is provided with an outer thread 23 on a part of its length. The helical thread track 19 of the support 11 exhibits a functionalized surface on which chemical or biological probes can be applied and immobilized using a loading device 13. The loading device 13 exhibits a tapering tip 24. The device 10 according to the invention once again includes a retainer 20 which exhibits an essentially cylindrical recess 21 which is provided with an inner thread 25 which is complementary to the outer thread 23 of the support 11. The flank depths of the inner thread 25 and of the outer thread 23 are selected such that, when the support 11 has been screwed in, a helical channel 26 is defined. A sample liquid, which can interact with the probes which are immobilized in the thread track 19, can be conveyed through the channel 26.

The device according to the invention exhibits means for conveying fluids, for the purpose of conveying the sample liquid and, where appropriate, other reaction liquids through the channel 26. In the case of the embodiment depicted in FIG. 2, the sample liquid is aliquoted into the recess 21 of the retainer 20. This can be effected by, for example, filling the recess 21 above the screwing-in aperture of the retainer 20 before the support 11 is screwed in. However, this can also be effected by means of a fluid duct 28 which opens out into the recess 21 in the region of the floor 27 of the retainer 20. The fluid duct is advantageously provided with a nonreturn valve 29 which prevents the sample liquid which is present in the recess 21 being displaced into the duct 28 when the support 11 is screwed in. The support 11 is now extended, in its lower region, by a displacement piston 300 which is sealed off toward the recess 21 by a sealing lip 30. If the outer diameter of the displacement piston 300 essentially corresponds to the inner diameter of the recess 21, it is also possible, when suitable materials are selected, to dispense with a sealing lip. A passage 31, whose one end opens out by way of an aperture 32 in the bottom region of the displacement piston 300 or the sealing lip 30 and whose other end opens out by way of an aperture 33 into the thread track 19 of the outer thread 23 of the support 11, is chased in the displacement piston. There is therefore a communicating connection between the thread track 19 and the recess 21 when the support is screwed in. Screwing in the support 11 presses the sample liquid out of the recess 21 and through the passage 31 and, after it has flowed out of the aperture 33, conveys it through the thread track 19. This consequently ensures that the sample liquid is able to come into contact with every target spot which is immobilized in the thread track 19.

Sucking-off arrangements (not shown here), which lead away the sample liquid after it has flowed through the thread track, can once again be provided in the upper region of the retainer 20.

The interaction of the probes which are immobilized in the thread track 19 and the substances in the sample liquid can be detected when screwing out the support 11. In this embodiment, an excitation and detection device 22, which is depicted diagrammatically and which in this case is integrated into the retainer, is provided for this purpose in the upper region of the retainer 20.

The support 11 is advantageously screwed in and screwed out automatically using a drive device 17 which can set the support 11 in rotation in both rotational directions, for example by way of a spindle 16.

As intimated in the diagram shown in FIG. 2, the retainer 20 can be constructed in a modular manner. For example, the retainer can exhibit an outer jacket 34 in which temperature-controlling devices are, for example, arranged. An inner jacket 35, which exhibits an inner thread which is specific for particular supports, is inserted into the outer jacket. In the same way, the retainer can exhibit an interchangeable bottom plate 36 such that it is possible to construct systems with and without fluid ducts or with one or more fluid ducts. The loading device 13 and the detection device 22 are also advantageously constructed in a modular manner.

Figure 3:
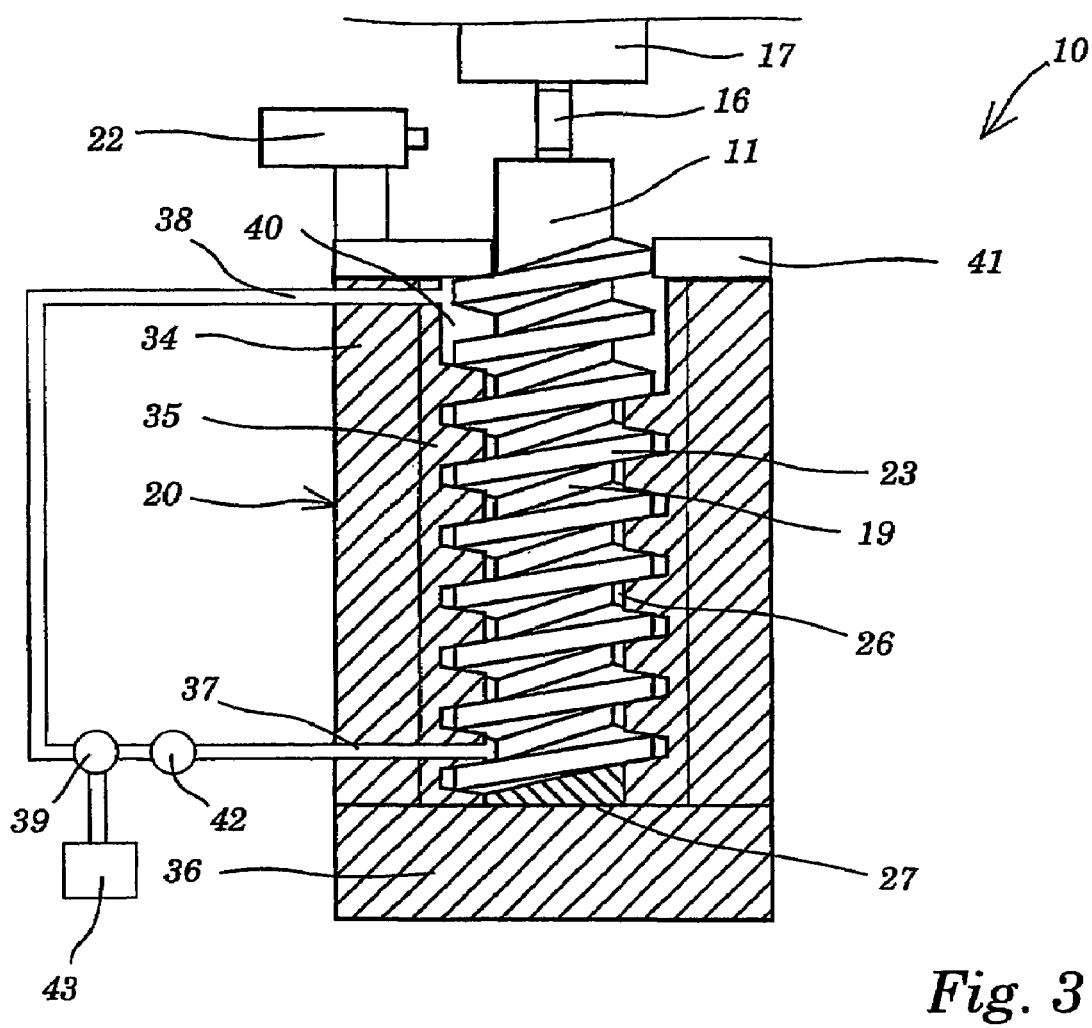
FIG. 3 shows a third embodiment of a device according to the invention.

FIG. 3 depicts a third embodiment of the device 10 according to the invention. In the embodiment shown in FIG. 3, the helically shaped support 11 is not used for displacing the sample liquid; instead, the support 11, which is coated with immobilized probes, is initially screwed completely into the retainer 20. When the support has been screwed in, a fluid duct 37 which has been chased in the bottom region of the retainer 20 communicates with the thread track 19. In addition, the embodiment provides a withdrawal duct 38 through which fluid can be pumped off from a collecting region 40 by way of a pump 42 and can be conveyed back by way of the duct 37. The retainer is sealed off in the upper region 41. A three-way valve 39 enables sample fluid to be fed in from a reservoir 43.

Figure 4:
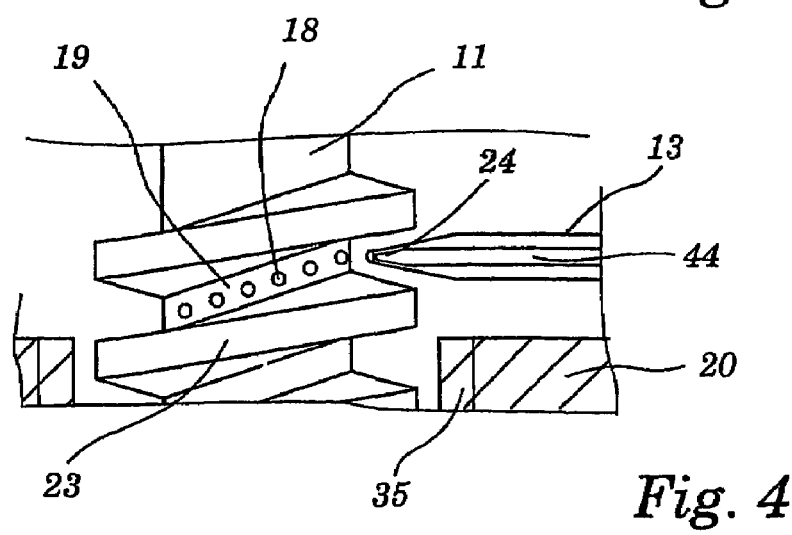
FIG. 4 shows an enlarged cutout depiction of the application of the probes in the device in FIG. 3.

FIG. 4 depicts a preferred variant of the loading of the target spots 18 into the thread track 19 of the support 11 in more detail. A fluid which contains substances which are being used as probes is first of all aspirated from a (not depicted) storage container into a channel 44 of the small capillary tube 13. The fluid is applied, in the form of minimally sized droplets, by way of the tip 24 to the functionalized thread 19 in order to form individual spots 18 on this thread.

However, the spots can also be loaded without any contact. For this, the small capillary tube is, for example, brought close to the thread without, however contacting it and delivers individual drops of the probe liquid by means of brief pressure surges. These pressure surges can, for example, be generated piezo-electrically.

Alternatively, the probes can also be introduced into the helical track in the form of with beads on which the probes are immobilized. In this connection, the beads, which typically have a diameter of from 1 μm to 1 mm, can be adhered in the thread or be clamped between the flanks of the thread.

Figure 6:
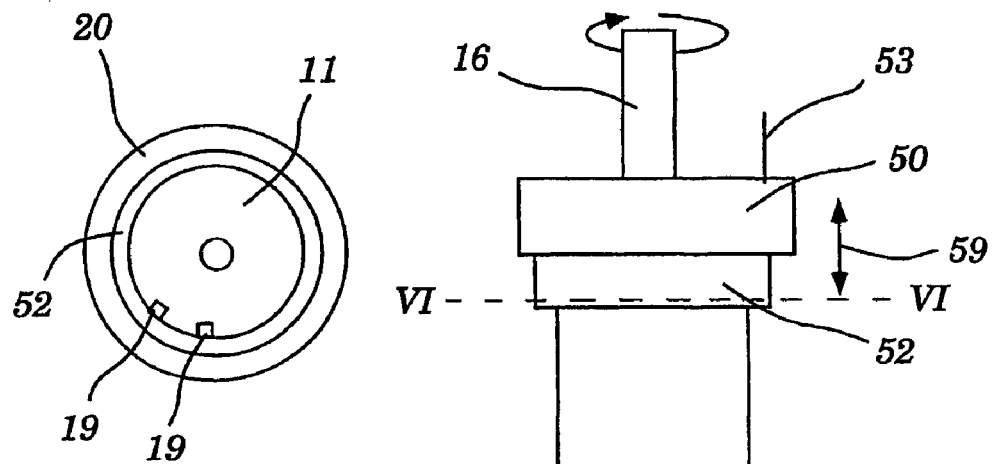
FIG. 6 shows a view from above onto the device shown in FIG. 5.
Figure 5:
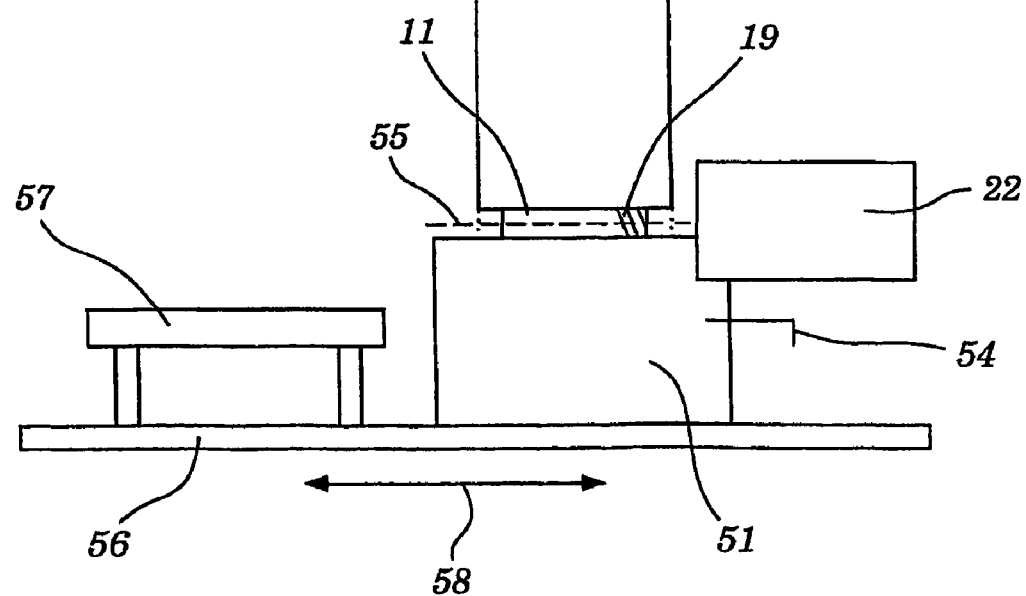
FIG. 5 shows a third embodiment of a device according to the invention which is particularly suitable for electrophoretic investigations.

FIGS. 5 and 6 depict a preferred variant of the support 11 which is suitable, in particular, for carrying out electrophoretic separation. FIG. 6 shows a cross section along the line VI-VI in FIG. 5. The device exhibits reservoirs 50, 51 for a buffer solution and a radial packing ring 52 for sealing off between the support 11 and the retainer 20. The samples which are to be separated electrophoretically are applied as spots, at one end of the support 11, to the tracks 19, which are, for example, filled with a gel, of the support 11. A high electrical voltage is applied, parallel to the longitudinal axis of the support 11, between the buffer reservoirs 50, 51 using electrodes 53, 54, which are shown diagrammatically in FIG. 5. As a result of having different charges and/or different mobilities, the individual constituents in the samples are separated in the gel such that they arrive at the other end of the support 11, for example at the level of the line 55, in a chronologically staggered manner and can be detected by a detection device 22. When a detection device, which is designed for optically detecting the sample constituents, is arranged outside the retainer 20, the retainer 20 can, in this region, exhibit a transparent window or a narrow slit. A ring 57 having an inner thread can be arranged on a common base plate 56 over a recess (which is not depicted here) in the base plate in order to remove the gel once again, after the electrophoresis, from the tracks 19 of the support 11. The arrows 58 and 59 indicate that the support 11 and the base plate 56 can be moved in relation to each other using positioning elements which are known per se (but which are not shown here) such that the support 11 can also be screwed automatically into the ring 57 after the electrophoresis has come to an end. In the variant depicted in FIGS. 5 and 6, two tracks 19 are provided on the support, which tracks run in a spiral path having a relatively large pitch. In this case, the inner wall of the cylindrical retainer 20 does not need to exhibit a complementary thread but can also be smooth in form instead.

Other variants of the support are depicted in FIGS. 7-10.

Figure 7:
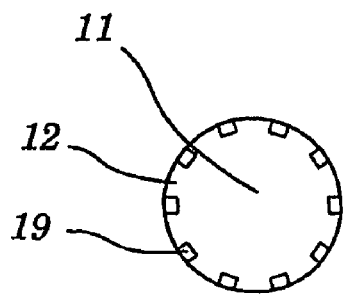
FIG. 7 shows a variant of a support for electrophoretic investigations, seen from above.
Figure 8:
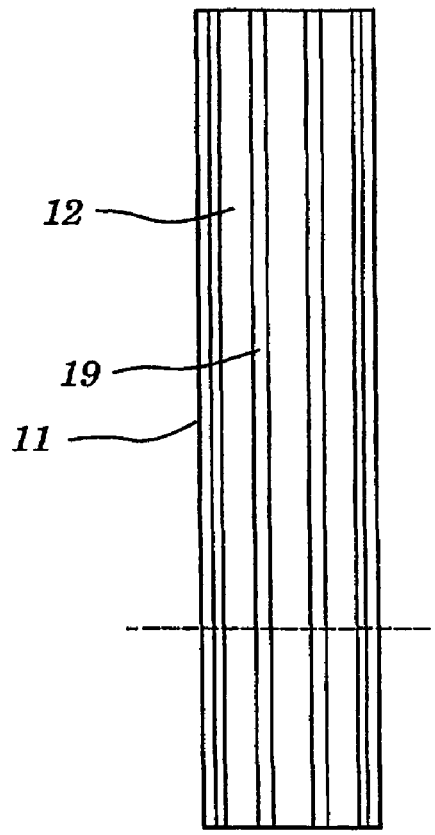
FIG. 8 shows the support shown in FIG. 7 in side view.

FIG. 7 shows a view from above and FIG. 8 shows a side view of another embodiment of the support 11. In this case, the tracks 19 are essentially arranged parallel to the longitudinal axis of the support 11. The flanks which bound the tracks laterally define a cylinder jacket 12 of the support such that the tracks 19 as it were constitute depressions in the cylindrical support 11. The support 11 can than be inserted into a retainer (not depicted here) which, like the retainer shown in FIG. 5, is provided with electrodes above and below the support. In this case, too, the retainer can exhibit a cylindrical inner space having smooth side walls. There is no need for an inner thread. After the support has been inserted into the retainer, the sample which is to be separated electrophoretically is loaded onto the upper end of the tracks 19 and a voltage is applied. The samples which are separated on the tracks 19 are then detected in the lower region of the retainer (as indicated by the broken line). Detection is therefore once again effected by measuring differences in the migration times of the individual constituents of the sample on the electrophoresis tracks. During the measurement, the support can be rotated about its longitudinal axis in order to analyze the individual tracks one after the other.

Figure 9:
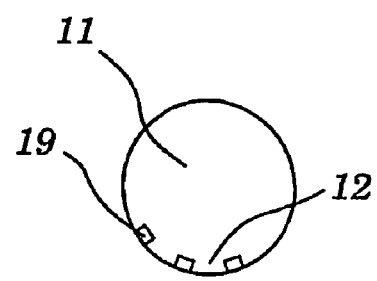
FIG. 9 shows another variant of a support for electrophoretic investigations seen from above.
Figure 10:
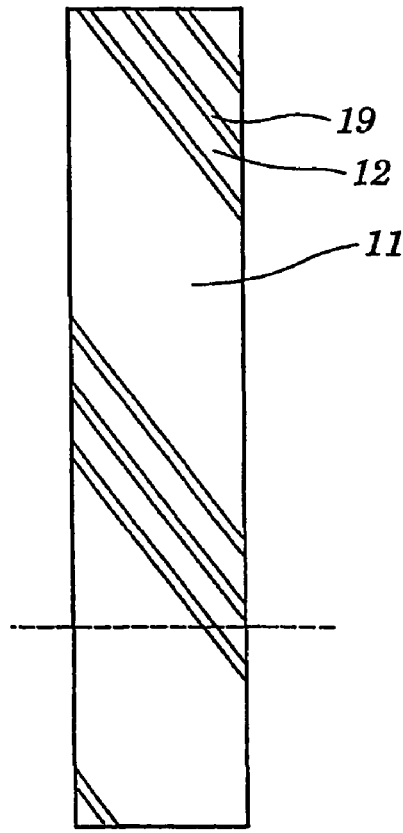
FIG. 10 shows the support shown in FIG. 9 in side view.

FIGS. 9 and 10 show a variant of the support shown in FIGS. 7 and 8 in which the tracks 19 are inclined relative to the longitudinal axis of the support. In this way, it is possible to increase the electrophoretically utilizable migration distance of the individual tracks 19 without the overall measurements of the system being increased.

FIGS. 11 to 14 depict another variant of the support 11 of the device according to the invention for analyzing chemical or biological samples. Once again, the support 11 possesses a general form which is helical in shape and in which individual sample spots are distributed along a helical thread track 19. In contrast to the previous examples, the sample spots are not applied to the basal surface of the thread track 19. Instead, the support 11 exhibits drill holes 61 in the thread track 19, which drill holes 61 are orientated radially to the longitudinal axis 60 of the support 11 and open out into a central drill hole 62 which is chased along the longitudinal axis 60. The radial drill holes 61 therefore constitute a communicating connection between the thread 19 and the central drill hole 62 as can be seen, in particular, from the detail view shown in FIG. 13. The diameter of the drill holes 61 is preferably in the range from 1 μm to 1 000 μm and very particularly preferably in the range of 50-200 μm. The length of the drill holes 61, which are not depicted true to scale in the drawing, is typically in the millimeter range.

Suitable capillary needles or similar loading devices can be used to fill the individual drill holes 61 individually with a sample fluid, which is retained in the drill holes by means of capillary forces. The droplets 63 of sample fluid which are present in each drill hole 61 can be brought into contact, and mixed, with other fluids by way of the thread track 19 and/or the central drill hole 62. Depending on the quantity of the sample fluid 63 which has been metered in to the individual drill holes, an air cushion 66 or 67, respectively, which initially prevents the fluids being mixed, is formed between the fluid 64 which is present in the thread 19 and the fluid 65 which is present in the central drill hole 62. A sequential mixing of the sample fluid 63 with the fluids 64 and 65, respectively, can be brought about at defined times in dependence on the regulation of the pressure difference in the fluids in the central drill hole 62 and in the thread 19, respectively. In the diagram shown in FIG. 13, the contact angles of the fluids are depicted such as corresponds, for example, to an aqueous fluid in a hydrophobized drill hole 61.

FIG. 14 depicts an exemplary arrangement of a variant of the support 11 shown in FIG. 11 in a retainer 20. It is also demonstrated, in the embodiment shown in FIG. 14, that the support 11 is particularly suitable for absorption measurements. For this, an optical waveguide 68, which, on a level with a detector 69 which is integrated into the retainer 20, exhibits an angled facet which radiates light radially in the direction of the detector 69, can, for example, be introduced into the central drill hole 62. If the individual drill holes 61 allow this radial light beam to pass through, absorption measurements can be carried out on the fluid which is present in the drill hole. The device shown in FIG. 14 also demonstrates that the retainer 11 can be provided with a conically shaped stopper 70 which is designed to be complementary to the upper edge 71 of the retainer 20 and which seals this edge when the support is screwed in. It is naturally possible for the retainer 20 to be sealed in this way in the embodiments of the device according to the invention which have previously been described with reference to FIGS. 1-10.

The stopper stopper 70 can also be designed as a radial packing ring which can be connected to the retainer 20 by way of a union nut or a thread, for example, and in which the shaft of the support 11 is freely rotatable such that, with the retainer being tightly sealed, the support 11 can move past the detector 69. In order to prevent variations in pressure in the liquid in the complementary thread of the retainer 20 when the support 11 moves, the retainer 20 can exhibit, in its upper region, an outlet 72 which is linked, by way of an equalizer 73, with an inlet 74 in the lower region of the retainer. The lower region of the retainer 20 is then once again designed as a radial packing ring 75.

The embodiment of the device according to the invention as shown in FIGS. 11-14 is suitable, in particular, for stopped-flow experiments with a high degree of time resolution and a high degree of sampling. In this case, it is possible, for example, to introduce identical samples into the drill holes 61 and to start a reaction by applying pressure at a defined point in time. Since the reaction begins at the same time in all the drill holes 61, a sequential analysis of the individual drill holes (for example on rotating the support 11 out of the retainer 20), constitutes a time-resolved measurement of the reaction kinetics. In the same way, it is possible to carry out highly parallel stopped-flow experiments, for example when different samples are introduced into the individual drill holes.

The device according to the invention is also particularly suitable for carrying out mixing assays using two or more different reaction solutions.

It is also possible to carry out what are termed hot-start experiments by isochronously mixing using the air cushions which are expelled by pressure pulses.

Another preferred area of application for the device shown in FIGS. 11-14 is in the area of what are termed flush-through assays or flush-through arrays. It is possible to increase the sensitivity in experiments of this nature by immobilizing a relatively large quantity of sample on the inner wall of the drill holes 61 and having a sensitive detection, by means of having a long detection path in the drill hole in the case of absorption measurements, for example.

In the case of the support shown in FIG. 11, the central drill hole can also be sealed using a slide-in core (not shown in the drawings) such that the support 11 is designed as a type of microtiter plate (or submicrotiter plate) having helically arranged wells. In this case, the outer diameter of the (where appropriate heatable) core essentially corresponds to the inner diameter of the drill hole 62. The core can naturally also have a somewhat smaller diameter such that the central drill hole 62 does not have to be completely filled with fluid but only has to be filled in a narrow ring (not shown in the drawings) [lacuna] core and the inner wall of the drill hole 62.

Since a rapid and efficient change in temperature in the thread track 19 and the radial drill holes 61 can be achieved by a change of medium within the central drill hole 62, specific loading of the drill holes 61 also makes it possible to carry out a highly parallel, rapid and effective PCR (polymerase chain reaction). For this, the PCR reaction mix is introduced into the wells by way of the central drill hole 52, or the central channel, which is constituted such that it can contain from a few microliters, or even less, up to several milliliters. In a conventional PCR, this PCR reaction mix consists of buffer solution, DNA polymerase, a set of DNA primers and the dNTPs which are required for synthesizing the counterstrands. In the case of quantitative PCR (Taq Man®, trademark belonging to the company Applied Biosystems, Foster City, Calif.), use is made of a special primer pair each member of which carries a different dye label which exhibits fluorescence characteristics in solution or in the annealing phase which differ from those after strand duplication, thereby providing information on the progress of the PCR. A simpler principle is that of using intercalation dyes to detect the products resulting from the PCR directly. The status of the PCR is registered simply by measuring the fluorescence intensity. The template DNA, that is the sequence which is in each case to be amplified, is supplied by pipetting it into the drill holes 61 which are filled with PCR solution and subsequently reducing the pressure in the central drill hole in order to retract the PCR mixture into the well. After liquid (e.g. deionized water) has been pumped through, this thereby encloses an air bubble, which prevents any dilution or contamination of the PCR mixture in the thread channel, in the thread channel 19 at the end of the drill hole 21 toward the thread track. The temperature cycling can now begin. For quantitative PCR, the wells are conveyed, after each cycle, past a fluorescence detector which is integrated into the retainer 22 and the instantaneous fluorescence intensity is measured and stored. Short pulses by way of the central liquid can be used to increase blending and, possibly, shorten reactivity or reaction times. For preparative purposes, the amplified DNA solution can be removed after the liquid in the thread has been pumped off and the screw has been withdrawn from the retainer.

Although a support having a central drill hole 62 and radial drill holes 61 has only been presented here for the case of a helically shaped support 11, it will be understood that, in principle, the previously presented variants of the support 11, for example those shown in FIGS. 5-9, can also be provided with radial drill holes, which open out into a central drill hole, instead of with the spots 18.

In that which follows, an application example which can be carried out in all the embodiments of the device according to the invention is explained in more detail.

EXAMPLE

Hybridizing DNA Arrays

System Parameters:

With a selected support radius of 5 mm and a channel width of 50 μm and the thread pitch being 0.1, 32 mm of channel length are obtained per revolution. 320 targets can be introduced into such a channel per revolution, giving 32 000 spots in the case of a thread bar of 1 centimeter in length. The customary length is several centimeters, which means that several hundred thousand samples can be deposited. The spot length density is 20 per centimeter of the channel. With a customary channel height of 10 μm, the channel volume becomes 15 μl per centimeter of channel length.

Preparing the System, Hybridizing and Reading the Fluorescence:

The support is inserted into the retainer. The support-retainer thread system is flushed with degassed, double-distilled [lacuna] which has been sterilized by filtration. It is then rewashed with a 70%-30% ethanol-water solution in order to remove microbubbles of gas and to achieve sterility. After that, coupling reagents are flushed through the channel, thereby functionalizing the channel in correspondence with the support material. Nitrocellulose methanol solution (NC solution) can be used as an all-purpose reagent. After the NC solution has been passed through, the support is withdrawn from the retainer. In connection with this, a suitable pin can be inserted into the channel track in order to generate a defined loading thickness. After the tracks have dried, the DNA targets are loaded (spotting) as the support is being inserted. At present, the solid pin technology is being used for this purpose. For this, use is made of several pins which are arranged in a row. The pins are located at an interval of approx. 4.5 millimeters, which interval is matched to the particular channel distance so as to ensure problem-free insertion into the channel track. If the support seals off the retainer tightly after insertion, 100% ethanol is then conducted in. After that, the ethanol is displaced with buffer solution thereby making it possible to introduce buffer in a bubble-free manner. A start is now made in setting the temperature of the support-retainer system; in this connection, temperatures are set in the range of 20-68° C. depending on the length of the DNA target. Probe DNA is now pumped in and, in connection with this, hybridized (see under A. and B.).

After the hybridization, washing with buffer takes place once again and, after that, the support is withdrawn from the retainer. As this is being done, the channel track is read using a fixed, ultrasensitive fluorescence detection system and the results are recorded by a data system. For the purposes of analytical certainty, several, as a rule two, spots of a target sequence are loaded on, which spots [lacuna] loaded at a variable distance which is known to the evaluation algorithm. On being analyzed, the spots are compared with identical DNA and the quality and reproducibility of the hybridization thereby tested. If the quality is not in a predetermined range, this spot is then banned from any further evaluation. In this way, high data quality is achieved selectively.

In order to make the support ready for a fresh cycle of analysis, the support is inserted into the retainer and flushed with a cleaning solution (bleach). It is then washed with water and buffer and the pH is measured. If necessary, the channel track can also be cleaned mechanically using a pin. For safety, the channel track is also scanned optically by the detection system, and the quality of the channel track established, before a fresh analytical procedure is carried out; depending on the circumstances, a fresh cleaning cycle may be necessary.

A. Probe Labeling

Total RNA was prepared (Chomczynski P. and Sacchi N, Anal. Biochem. 1987 162(1), 156-159) and used for isolating poly(A) RNA with the aid of (oligo-dT)-Dynabeads (Dynal AS, Oslo, Norway) in accordance with the manufacturer's instructions. For primer annealing, 2 μg of the resulting poly (A) RNA, together with 6 μl of oligo(dT)$_{21}$ (50 μmol/l; ARK Scientific Biosystems GmbH, Darmstadt), were made up to 15 μl with DEPC-treated water, after which this mixture was heated at 70° C. for 5 min and then cooled on ice. 6 μl of 5× first strand buffer (Life Technologies GmbH, Karlsruhe; 250 mmol of Tris-HCl/l, pH 8.3; 375 mmol of KCl/l; 15 mmol of MgCl$_2$/l), 1 μl of RNase inhibitor (Roche Molecular Biochemicals, Mannheim), 100 mmol of dithio-threitol (Life Technologies GmbH, Karlsruhe), 0.6 μl of 50× dNTP-T (in each case 25 mmol/l dATP, dCTP and dGTP; 10 mmol of dTTP/l; Roche Molecular Biochemicals, Mannheim), 2 μl of Cy3-dUTP or Cy5-dUTP (1 mmol/l; Amersham-Pharmacia Biotech Europe GmbH, Freiburg) and 2 μl of Superscript II (200 units/μl; Life Technologies GmbH, Karlsruhe) were then added. The fluorescence-labeled first-strand cDNA was then synthesized at 42° C. for 2 hrs in a preheated Thermocycler. In order to denature the RNA, 2.5 μl of 1N NaOH were added and the mixture was heated at 65° C. for 10 min. After it had been cooled down on ice, it was neutralized with 6.2 μl of 1 mol/l Tris-HCl, pH 7.5, diluted with TE buffer (10 mmol of Tris-HCl/l, 1 mmol of EDTA/l, pH 8.0) to 400 μl and concentrated down on a Microcon-30 column (Millipore GmbH, Eschborn; centrifugation at 13 000 rpm for 10 min) to 10 μl.

B. Hybridizing

For the hybridization, 5 μl each of Cy 3-labeled cDNA and Cy 5-labeled cDNA were mixed with each other and then treated with 50 μl of hybridization buffer (0.25×SSC, 0.02% SDS, 1% N-lauroylsarcosine, 1% blocking reagent (Roche Molecular Biochemicals, Mannheim), 1 μg of human C$_{ot}$1 DNA (Life Technologies GmbH, Karlsruhe)). This hybridization solution was denatured at 95° C. for 2 min in the Thermocycler, after which the temperature was reduced to 50° C. and hybridization was carried out for 14 hrs. The hybridization solution was removed and the tubes were washed 3×5 min at room temperature with 2×SSC/0.1% SDS, followed by 3×5 min with 0.2×SSC/0.1% SSC at 42° C. and, in conclusion, 1×5 min with 0.1×SSC/0.1% SDS at 42° C.

The invention claimed is:

1. A device for analyzing chemical or biological samples, comprising:
   a support having a substantially cylindrical jacket surface on which is provided at least one helically threaded track, wherein chemical or biological targets or samples are immobilized in the at least one helically threaded track, and
   a retainer having a substantially cylindrical recess, said support being insertable into said recess to form at least one fluid channel defining a reaction volume between said support and an inner surface of said recess.

2. The device as claimed in claim 1, comprising means for conveying fluids through said at least one channel.

3. The device as claimed in claim 2, wherein said means for conveying fluids comprises at least one fluid reservoir and one pumping device.

4. The device as claimed in claim 2, wherein said means for conveying fluids are formed by said support, defining a piston, and said retainer recess, defining the fluid reservoir.

5. The device as claimed in claim 4, wherein said support comprises a threadless cylindrical section having an outer diameter that substantially corresponds to the inner diameter of said retainer recess.

6. The device as claimed in claim 5, wherein a passage is provided in said threadless cylindrical section, said passage communicating with said threaded track of said support.

7. The device as claimed in claim 1, wherein a central aperture is provided in the support and radial apertures communicating with said central aperture are provided in the jacket surface of the support.

8. The device as claimed in claim 1, comprising means for applying the targets or samples in the form of individual defined spots or fluid droplets.

9. The device as claimed in claim 1, wherein said cylindrical recess in the retainer includes a complementary counterthread relative to the helically threaded track of the support such that after the support and the retainer are coupled, a channel, through which fluid can be conveyed, is formed along the complementary counterthread.

10. The device as claimed in claim 1, wherein the thread of said thread track is selected from the group consisting of rectangular threads, trapezoidal threads, metric ISO threads as defined by the International Organization for Standardization, round threads and pipe thread.

11. The device as claimed in claim 1, wherein said retainer comprises an excitation and detection device for analyzing said chemical or biological targets or samples.

12. The device as claimed in claim 11, wherein said excitation and detection device is integrated into said retainer.

13. The device as claimed in claim 12, wherein said excitation and detection device is arranged adjacent to an opening to the recess of the retainer.

14. The device as claimed in claim 13, wherein the detection device comprises means for measuring any of chemiluminescence signals, fluorescence signals, absorption signals and radioactivity.

15. The device as claimed in claim 1, wherein the chemical or biological samples to be analyzed are DNA or RNA.

16. The device as claimed in claim 1, comprising drive means for inserting the support into the retainer and for withdrawing the support from the retainer.

17. The device as claimed in claim 1, wherein said cylindrical recess in the container is provided with a smooth inner wall.

18. The device as claimed in claim 1, wherein said threaded track is filled with a gel.

19. The device as claimed in claim 18, further comprising a means for electrophoretic analysis.

20. The device as claimed in claim 1, wherein the reaction volume is further defined between said helically threaded track of said support and the inner surface of said recess.

* * * * *

UNITED STATES PATENT AND TRADEMARK OFFICE
CERTIFICATE OF CORRECTION

PATENT NO. : 7,455,967 B2  Page 1 of 1
APPLICATION NO. : 10/333884
DATED : November 25, 2008
INVENTOR(S) : Ralph Muller It is certified that error appears in the above-identified patent and that said Letters Patent is hereby corrected as shown below:

On the Title page of the patent, please replace:

[65]         Prior Publication Data
US 2004/0053327 A1     Mar. 18, 2004 with:

Item [65]         Prior Publication Data
US 2004/0053327 A1     Mar. 18, 2004

Item [30]         Foreign Application Priority Data
July 25, 2000 (DE)         100 36 174.9

Signed and Sealed this

Seventh Day of July, 2009

JOHN DOLL
*Acting Director of the United States Patent and Trademark Office*